(12) United States Patent
Iwamoto

(10) Patent No.: US 7,908,144 B2
(45) Date of Patent: Mar. 15, 2011

(54) INFORMATION PROCESSING SYSTEM AND INFORMATION PROCESSING METHOD

(75) Inventor: Takashi Iwamoto, Chiba (JP)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 12/641,991

(22) Filed: Dec. 18, 2009

(65) Prior Publication Data

US 2011/0022392 A1    Jan. 27, 2011

(30) Foreign Application Priority Data

Jul. 27, 2009    (JP) .................................. 2009-174642

(51) Int. Cl.
*G10L 11/00* (2006.01)
(52) U.S. Cl. ...................................... 704/270; 704/200
(58) Field of Classification Search ........................ None
See application file for complete search history.

(56) References Cited

U.S. PATENT DOCUMENTS

| | | | | |
|---|---|---|---|---|
| 6,151,571 | A |  | 11/2000 | Pertrushin |
| 7,191,134 | B2 | * | 3/2007 | Nunally ........................ 704/270 |
| 7,321,855 | B2 | * | 1/2008 | Humble ........................ 704/270 |
| 7,356,468 | B2 | * | 4/2008 | Webster ........................ 704/258 |
| 2010/0211394 | A1 | * | 8/2010 | Nazdratenko ................. 704/270 |

FOREIGN PATENT DOCUMENTS

| | | |
|---|---|---|
| JP | 2002-314715 | 10/2002 |
| JP | 2003-508805 | 3/2003 |
| JP | 2006-262231 | 9/2006 |
| JP | 2007-000366 | 1/2007 |
| JP | 2008-015561 | 1/2008 |
| WO | WO 01/16938 | 3/2001 |

OTHER PUBLICATIONS

Notice of Reasons for Rejection for JP 2009-174642 mailed Aug. 27, 2009 (with English translation).
"A comparison between Tokyo and Osaka," http:/www.stresscare.com/info/report/prorep102.html, STRESSCARE.COM (with English translation) (at least Mar. 16, 2010).
Office Action for Japanese Patent Appl. No. 2009-174642 mailed Feb. 12, 2010 (with English translation).
"A comparison between Tokyo and Osaka," http:/www.stresscare.com/info/report/prorep102.html, STRESSCARE.COM (with English translation) (Jul. 16, 2009) (previously submitted but date revised).
"National Institute for Truth Verification", retrieved May 3, 2010, from online, http://www.cvsa1.com/index.htm, NITV Official Website.

* cited by examiner

*Primary Examiner* — Brian L Albertalli
(74) *Attorney, Agent, or Firm* — Foley & Lardner LLP

(57) ABSTRACT

A framework is provided which performs location-based analysis using an individual feature such as a stress level obtained based on biological information. An information processing system includes an acquisition unit which acquires frequency power information of a voice inputted at a mobile terminal having a voice communication function, and position information of a base station device that relayed voice communication of the mobile terminal when the voice was inputted; a storage unit which stores the acquired frequency power information and the acquired position information in association with each other; an acceptance unit which accepts designation of an area; and an output unit which identifies the position information related to the designated area, acquires the frequency power information associated with the identified position information with reference to the storage unit, obtains a stress level of a user of the mobile terminal in the designated area based on frequency power information of a frequency greater than or equal to a threshold value within the acquired frequency power information, and outputs the stress level in association with the designated area.

7 Claims, 6 Drawing Sheets

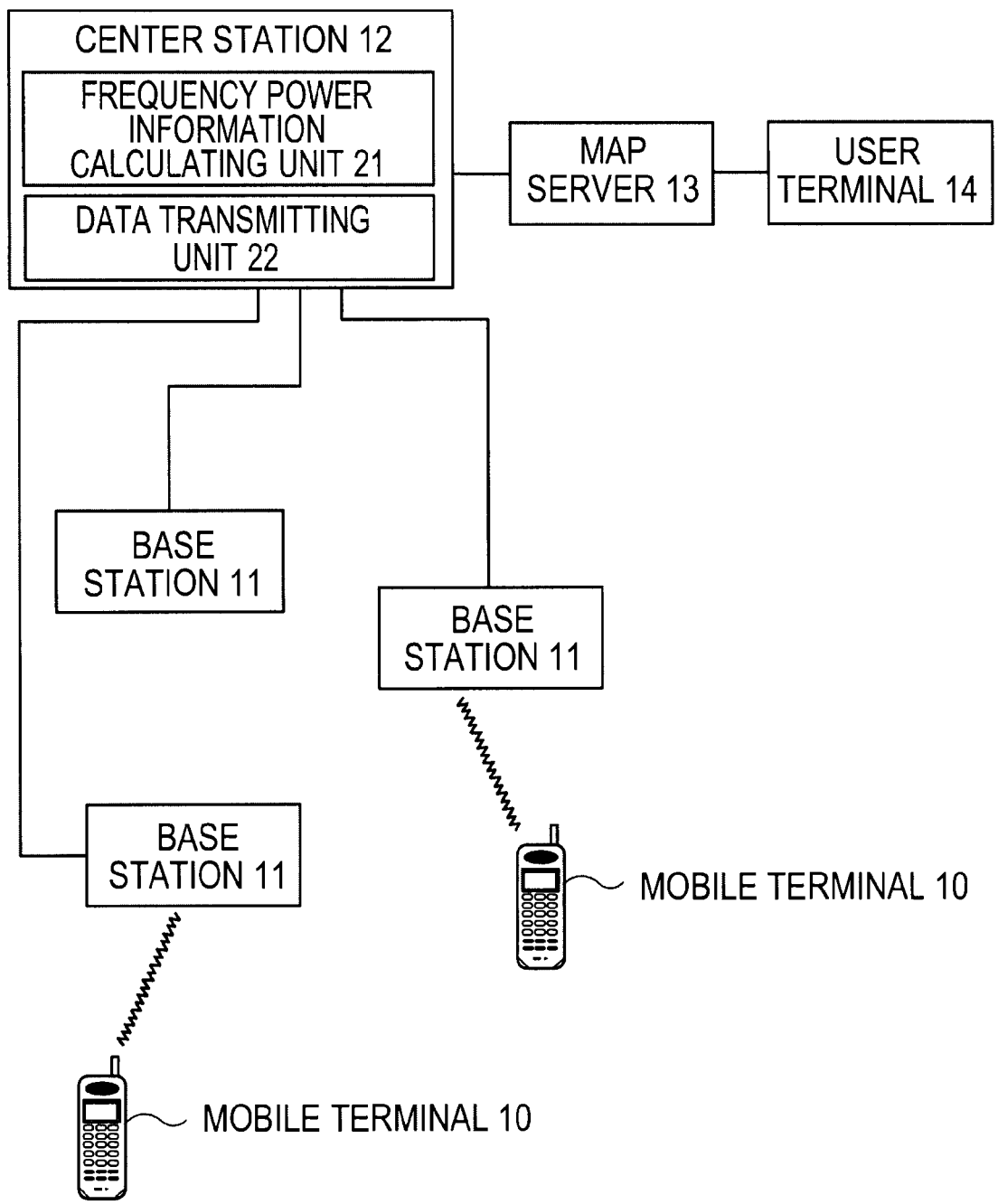

| AVERAGE OF MEAN POWER SPECTRAL DENSITIES | STRESS LEVEL |
|---|---|
| 0 ~ 500 | 1 |
| 500 ~ 1000 | 2 |
| 1000 ~ 2000 | 3 |
| 3000 ~ | 4 |

# INFORMATION PROCESSING SYSTEM AND INFORMATION PROCESSING METHOD

CROSS REFERENCE TO RELATED APPLICATION

This application claims the benefit of Japanese Application No. 2009-174642 filed on Jul. 27, 2009 which is incorporated herein by reference.

BACKGROUND OF THE INVENTION

1. Field of the Invention

The present disclosure relates to an information processing system and an information processing method using biological information.

2. Description of the Related Art

In recent years, because stress in people's social lives has significantly increased, physical and mental disorders due to stress are a big problem even at the social level.

The degree of stress needs to be measured in order to deal with the stress appropriately. Until now, there have been developed and proposed technologies to measure a stress level using information acquired from a living body (biological information) such as pulse, blood pressure, perspiration, electrocardiogram, brain wave, and voice.

For example, see "National Institute for Truth Verification", Retrieved Jul. 16, 2009 from online, http://www.cvsal.com/index.htm.

Conventionally, an individual feature such as a stress level obtained based on biological information is used for counseling for an individual from which the biological information has been acquired, improvement of the individual environment, and the like.

However, factors casing stress are not limited to factors dependent on personal aspects, but include many factors dependent on locations.

In addition, some of individual features obtained based on individual biological information can vary not only due to an individual factor but also due to a regional factor as in the case of stress level.

Thus, there is desired a framework which performs location-based analysis using an individual feature such as a stress level obtained based on biological information.

SUMMARY OF THE INVENTION

An information processing system of the present disclosure includes: an acquisition unit which acquires frequency power information of a voice inputted at a mobile terminal having a voice communication function, and position information of a base station device that relayed voice communication of the mobile terminal when the voice was inputted; a storage unit which stores the acquired frequency power information and the acquired position information in association with each other; an acceptance unit which accepts designation of an area; and an output unit which identifies the position information related to the designated area with reference to the storage unit, acquires the frequency power information associated with the identified position information, obtains a stress level of a user of the mobile terminal in the designated area based on frequency power information of a frequency greater than or equal to a threshold value within the acquired frequency power information, and outputs the stress level in association with the designated area.

An information processing system of the present disclosure includes: an acquisition unit which acquires biological information of a user or processed information of the biological information, and position information of the user at a time when the biological information was generated; a storage unit which stores the acquired biological information or processed information thereof and the acquired position information in association with each other; and a feature output unit which identifies the position information related to a predetermined area with reference to the storage unit, acquires the biological information or processed information thereof associated with the identified position information, obtains an individual feature about the user in the predetermined area based on the acquired information, and outputs the individual feature in association with the predetermined area.

The acquisition unit may acquire, as the processed information of the biological information of the user, frequency power information of a voice of the user which was inputted at a mobile terminal having a voice communication function, and acquire, as the position information of the user, position information of the mobile terminal at a time when the voice was inputted.

The acquisition unit may acquire, as the position information of the mobile terminal, position information of a base station device that relayed voice communication of the mobile terminal when the voice was inputted, or position information of the mobile terminal which is determined by a GPS function of the mobile terminal within a period determined based on the time when the voice was inputted.

The feature output unit may identify the position information related to the predetermined area, acquire the frequency power information associated with the identified position information with reference to the storage unit, obtain a stress level of the user of the mobile terminal in the predetermined area as the individual feature based on frequency power information of a frequency greater than or equal to a threshold value within the acquired frequency power information, and output the stress level in association with the predetermined area.

The feature output unit may output map information for displaying the individual feature in association with the predetermined area on a map or a layout diagram of an area including the predetermined area.

An information processing method of the present disclosure includes: acquiring frequency power information of a voice inputted at a mobile terminal having a voice communication function, and position information of a base station device that relayed voice communication of the mobile terminal when the voice was inputted; storing the acquired frequency power information and the acquired position information in association with each other in a memory; accepting designation of an area; and identifying the position information related to the designated area with reference to the memory, acquiring the frequency power information associated with the identified position information, obtaining a stress level of a user of the mobile terminal in the designated area based on frequency power information of a frequency greater than or equal to a threshold value within the acquired frequency power information, and outputting the stress level in association with the designated area.

Processing corresponding to the information processing method of the present disclosure can be performed by a CPU of a computer, and a program for the processing can be installed or loaded through various media such as a CD-ROM, a magnetic disk, a semiconductor memory, and a communication network.

The term "unit" as used herein includes a unit implemented by hardware, a unit implemented by software, and a unit implemented by both of them. One unit may be implemented by two or more pieces of hardware, and two or more units may be implemented by one piece of hardware.

BRIEF DESCRIPTION OF THE DRAWINGS

FIG. 1 is a block diagram showing a schematic configuration of an information processing system 1 of the present embodiment;

DETAILED DESCRIPTION OF THE PREFERRED EMBODIMENTS

Figure 2A:
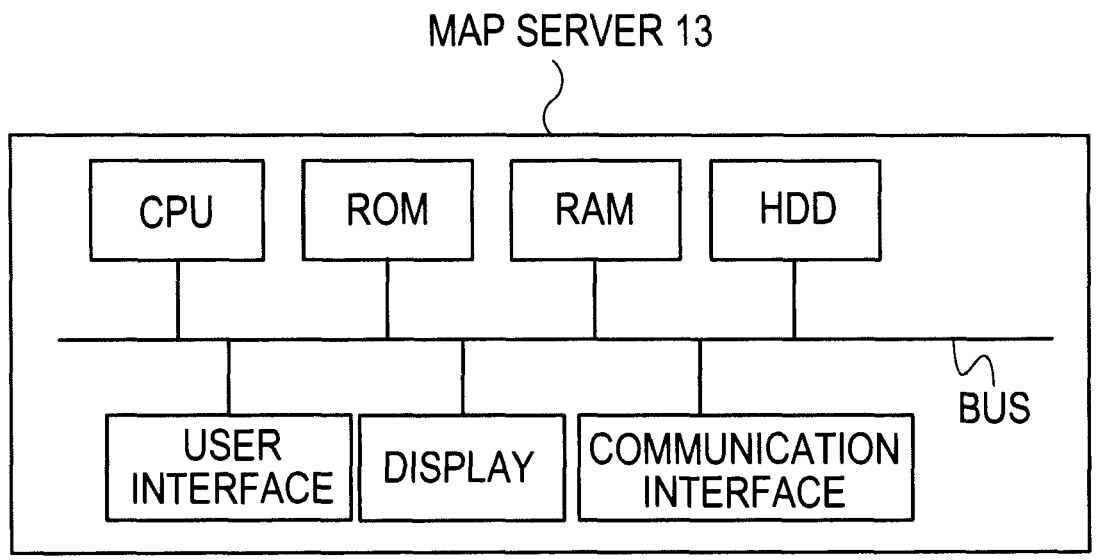
FIG. 2A is a diagram showing a hardware configuration of a map server 13 according to the present embodiment.

Hereinafter, a preferred embodiment for carrying out the present disclosure will be described with reference to the drawings. The present embodiment will be described using an exemplary case where a voice inputted to a mobile terminal and a power spectral density thereof are employed as biological information of a user and processed information of the biological information, and a stress level obtained based on frequency power information of the voice is employed as an individual feature about the user.

FIG. 1 is a diagram showing a schematic configuration of an information processing system 1 for outputting an area-specific stress level according to the present embodiment. As shown in FIG. 1, the information processing system 1 includes a plurality of mobile terminals 10, base stations 11 configured to be able to communicate with the mobile terminals 10, a center station (control station) 12 configured to be able to communicate with the base stations 11, a map server 13 configured to be able to communicate with the center station 12, a user terminal 14 configured to be able to communicate with the map server 13, etc.

The mobile terminals 10, the base stations 11, the center station 12, and the user terminal 14 may be provided as either a device inside the information processing system 1 or a device outside the information processing system 1. Although the center station 12, the map server 13, and the user terminal 14 are each shown as only one component in FIG. 1, a plurality of each of them may be provided depending on design. The user terminal 14 may be one of the mobile terminals 10.

As a general rule, the mobile terminals 10, the base stations 11, and the center station 12 have the same functional configurations as those of a conventional mobile communication system constructed with a PHS, mobile telephony, or the like. For example, the mobile terminals 10 have a function of performing voice communication with another mobile terminal 10 via the base stations 11, and the like, the base stations 11 have a function of relaying voice communication of the mobile terminals 10, and the like, and the center station 12 has a radio network controller function (RNC function), a circuit switching function, a packet switching function, a base station database function, and the like. As these mobile terminals 10, base stations 11 and center station 12, corresponding components of the existing mobile communication system can be used.

However, the center station 12 of the present disclosure has, in addition to the function of the center station of the conventional mobile communication system, a frequency power information calculating unit 21 which calculates a power spectral density [W/Hz] as frequency power information of a voice inputted at any mobile terminal 10, and a data transmitting unit 22 which transmits a power spectral density of a voice and position information of a user at a time when the voice was generated (the voice was inputted to the mobile terminal 10), to the map server 13.

The map server 13 has a function of outputting an area-specific stress level using a power spectral density of a voice inputted at the mobile terminal 10.

FIG. 2A is a block diagram showing a hardware configuration of the map server 13. As shown in FIG. 2A, the map server 13 can be composed of a general-purpose computer having hardware such as a CPU, memories (ROM, RAM), an HDD, a user interface, a display, a communication interface, etc.

Figure 2B:
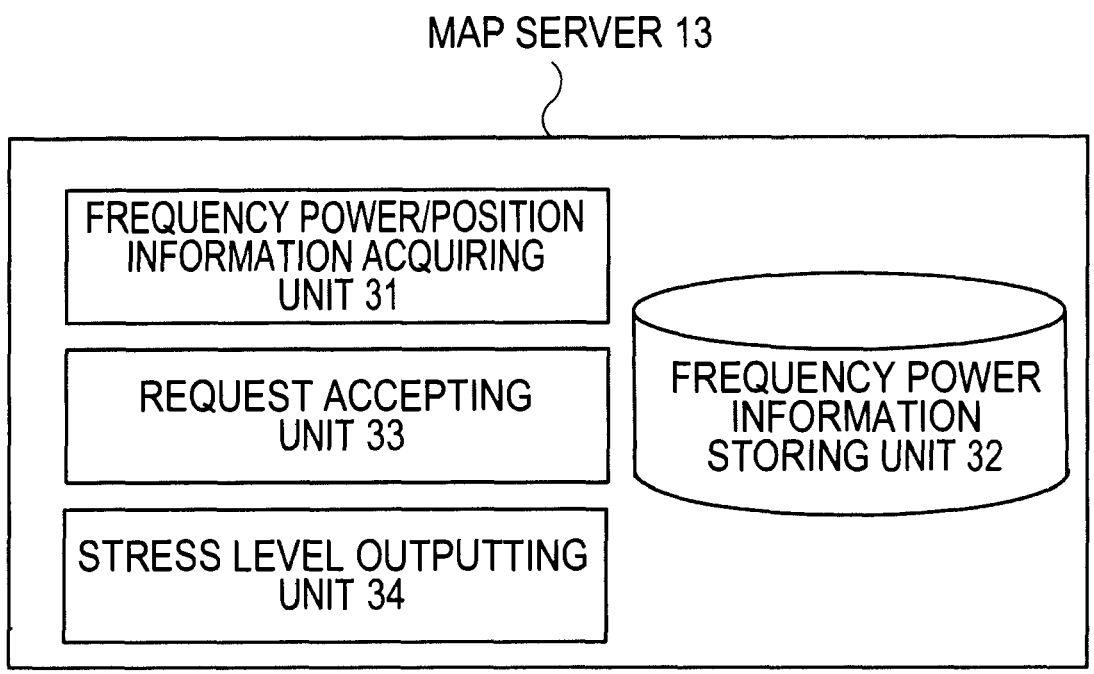
FIG. 2B is a diagram showing a functional configuration of the map server 13 according to the present embodiment.

FIG. 2B is a block diagram showing a functional configuration of the map server 13. As shown in FIG. 2B, the map server 13 includes functional units such as a frequency power/position information acquiring unit 31, a frequency power information storing unit 32, a request accepting unit 33, and a stress level outputting unit 34. Although the frequency power information storing unit 32 is configured as a part of the map server 13 in FIG. 2B, the frequency power information storing unit 32 may be under control of a different information processing device (such as a database server) because it just needs to be configured to be accessible directly or indirectly by the map server 13.

The map server 13 has functions which a typical Web server has, for example, a function of communicating with the user terminal 14 via a communication network, and these functions are implemented using a known technology.

The frequency power/position information acquiring unit 31 receives (acquires) power spectral density of a voice and voice input position information from the center station 12.

Figure 3:
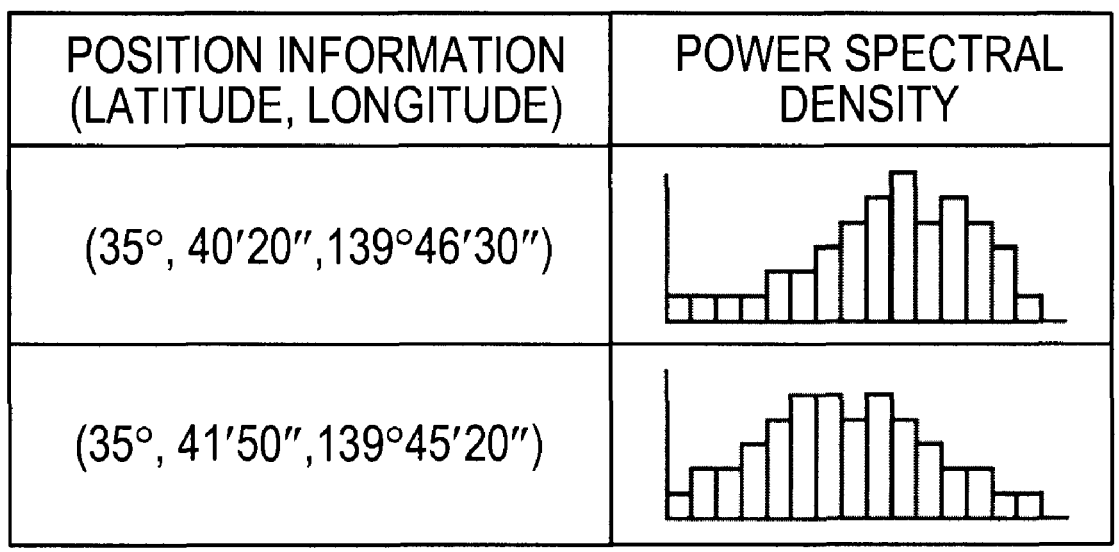
FIG. 3 is a diagram showing an example of a data structure of a frequency power information storing unit 32 according to the present embodiment.

The frequency power information storing unit 32 stores the power spectral density of the voice and the voice input position information acquired by the frequency power/position information acquiring unit 31 in association with each other. FIG. 3 schematically shows a data structure of the frequency power information storing unit 32. A conventional database technology such as a relational database can be used for data management in the frequency power information storing unit 32.

A request accepting unit 33 receives a stress level output request including area designation information from the user terminal 14.

When the request accepting unit 33 receives the stress level output request, the stress level outputting unit 34 identifies position information related to an area designated by the stress level output request, acquires power spectral densities associated with the identified position information with reference to the frequency power information storing unit 32, obtains a stress level of a user of the mobile terminal 10 in the designated area based on a power spectral density corresponding to a frequency greater than or equal to a threshold value among the acquired power spectral densities, and sends the stress level in association with the designated area to the user terminal 14.

The user terminal 14 includes an input/output device, and is configured to be able to accept an input from a user who uses the information processing system 1 and output information to the user. As this user terminal 14, a typical personal computer or mobile terminal can be used.

Figure 4:
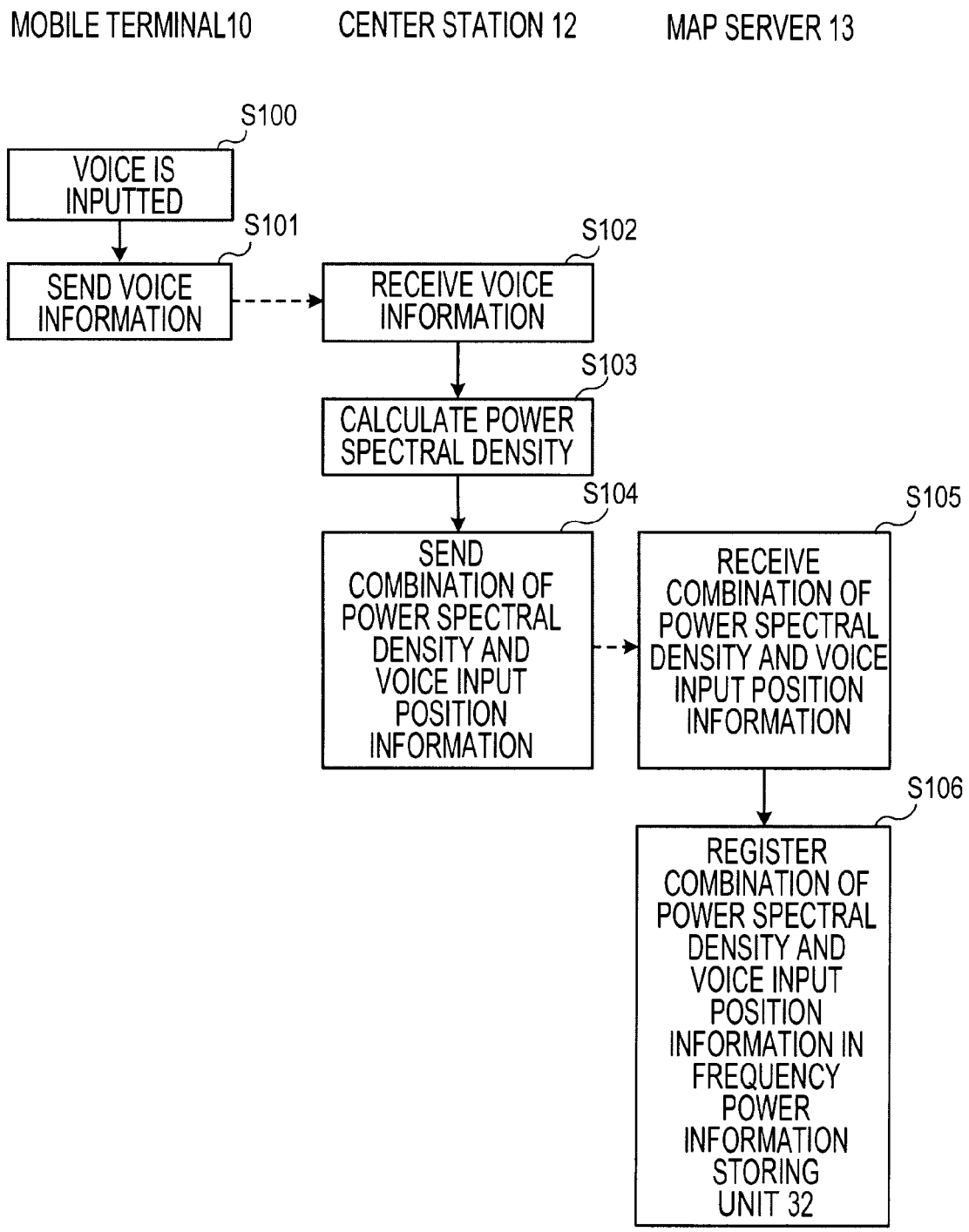
FIG. 4 is a flowchart illustrating an information collection phase according to the present embodiment.
Figure 5:
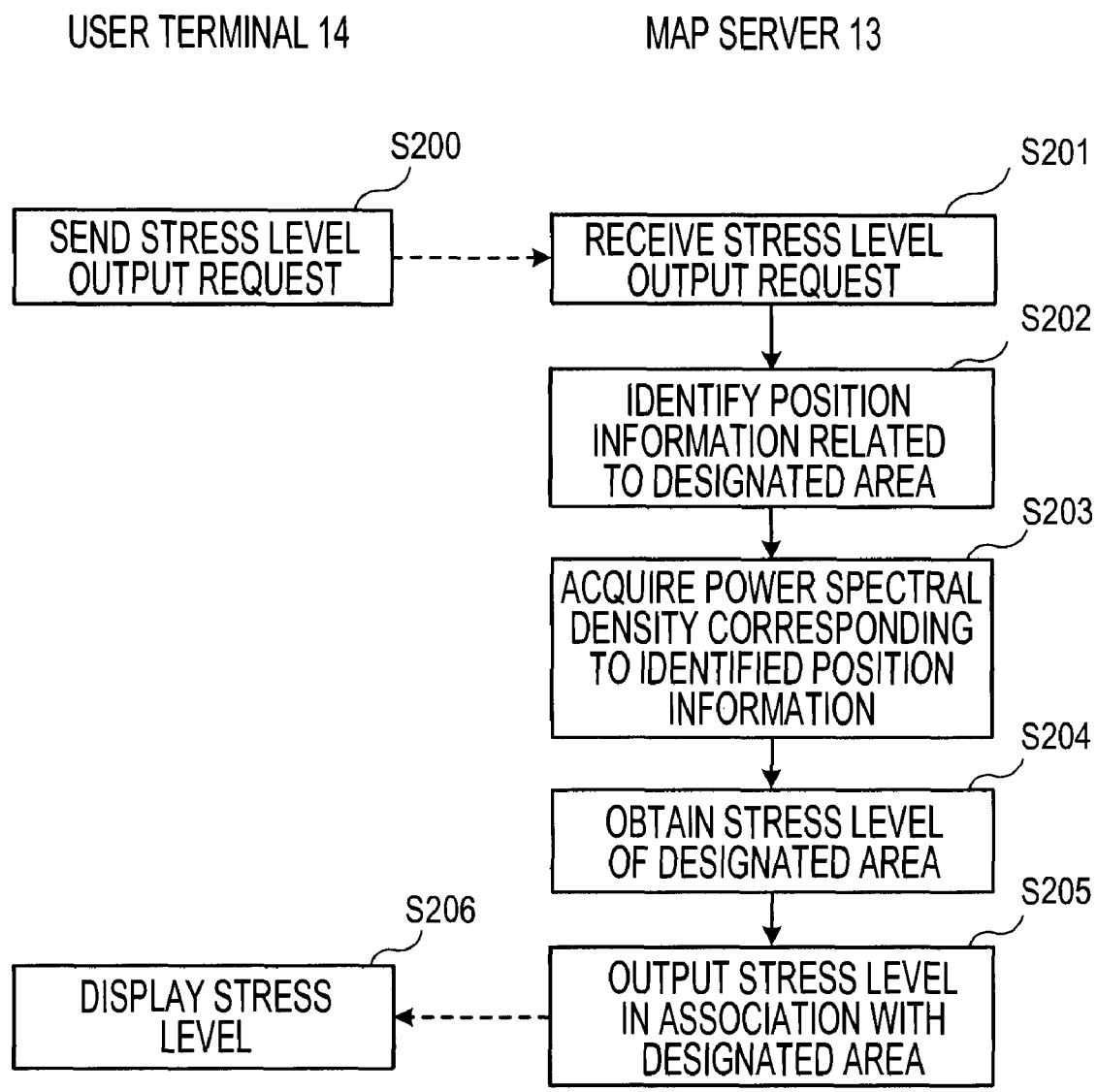
FIG. 5 is a flowchart illustrating a stress level output phase according to the present embodiment.

A framework implemented using the information processing system 1 will be described below with reference to flowcharts shown in FIG. 4 and FIG. 5. Any steps of the flowcharts (including partial steps having no reference numeral) may be executed in an arbitrarily modified sequence or in parallel unless processing of them causes inconsistency.

(Information Collection Phase: FIG. 4)

The Information collection phase is executed constantly or periodically during a voice communication being performed using the mobile terminal 10, or when a predetermined condition is satisfied (for example, when a user permits frequency power information of his/her voice to be collected).

In the information collection phase, when a user's voice is inputted to the mobile terminal 10 (S100), the inputted user's voice is converted to voice information to which predetermined coding is applied by the mobile terminal 10, and sent to the center station 12 via the relevant base station 11 according to a predetermined protocol (S101).

When the center station 12 receives the voice information (S102), the frequency power information calculating unit 21 calculates a power spectral density of the voice based on the received voice information (S103).

For example, if the mobile communication system using the mobile terminal 10, the base station 11, and the center station 12 employs a spectrum coding method or a method equivalent thereto as a voice coding method, a power spectral density of a voice can be calculated from spectral information included in a transferred signal. Alternatively, for example, if the mobile communication system employs a waveform coding method or a method equivalent thereto, a power spectral density of a voice can be calculated by obtaining a waveform of the voice based on a transferred signal and applying Fourier transform processing (e.g., FFT (Fast Fourier Transform)) to the waveform.

Then, the data transmitting unit 22 transmits the power spectral density of the voice and position information of the user at a time when the voice was generated (the voice was inputted to the mobile terminal 10) in association with each other to the map server 13 (S104).

In the present embodiment, position information of the base station 11 which relayed voice communication of the mobile terminal 10 when the voice was inputted to the mobile terminal 10 (hereinafter referred to as "voice input position information") is sent as position information of the user. If identification information of the relaying base station 11 is included in voice information received by the center station 12, the data transmitting unit 22 can acquire position information (latitude, longitude) of the relaying base station 11 by querying the base station database.

The data transmitting unit 22 may be configured to transmit in response to a request from the map server 13.

In the map server 13, when the frequency power/position information acquiring unit 31 receives (acquires) the combination of the power spectral density of the voice and the voice input position information sent from the center station 12 (S105), these combined information are registered in association with each other in the frequency power information storing unit 32 (S106). In a case where area designation is made using address information in a stress level output phase described later, position information (latitude, longitude) may be converted to position information (address) using conventional reverse geo-coding function or service, and registered in the frequency power information storing unit 32.

(Stress Level Output Phase: FIG. 5)

The stress level output phase is executed when a user inputs an area designation to the user terminal 14 after the information collection phase.

When the area designation is inputted, a stress level output request including area designation information is sent from the user terminal 14 to the map server 13 (S200).

According to a target area of stress level analysis, area designation information can include address information such as a prefecture, a city, a town and a village, information of an area name such as a park or a business establishment, a building name, a road name and a route name, information of an area identified by a latitude and a longitude, and the like. When the map server 13 can refer to a database of areas, area designation information may include area identification information which can be used in the database.

In addition, a user may input a plurality of area designations at the same time, and in this case, a stress level output request includes a plurality of area designation information.

In the present embodiment, since position information of the base station 11 is used as position information of the user, a zone or cell covered by the base station 11 defines a resolution of an area which can be designated. Therefore, for example, if a plurality of base stations are arranged in one building or business establishment (i.e. it is covered by a plurality of base stations), an area can be designated for each base station's coverage within the one building or business establishment.

In the map server 13, when the request accepting unit 33 receives the stress level output request sent from the user terminal 14 (S201), the stress level outputting unit 34 identifies position information of the base station 11 related to the designated area among position information registered in the frequency power information storing unit 32 based on the area designation information included in the stress level output request (S202).

For example, if an area is designated using a prefecture and a city, a town or a village, position information of the base station 11 which is within the designated area is identified. For another example, if an area is designated using a road or a route, position information of the base station 11 which is within a predetermined distance from the designated area is identified. If information of a zone or cell of each base station 11 can be acquired by the map server 13, position information of the base station 11 corresponding to the zone or cell through which the designated road or route passes may be identified.

Then, the stress level outputting unit 34 acquires a power spectral density corresponding to the identified position information with reference to the frequency power information storing unit 32 (S203).

Then, the stress level outputting unit 34 obtains a stress level of the user of the mobile terminal 10 in the designated area based on the acquired power spectral density (S204).

Various conventional techniques such as voice stress analysis and voice emotion analysis may be used to obtain a stress level from a power spectral density. However, in the present embodiment, a greater power spectral density at high frequencies is determined to indicate a higher stress level based on the findings that as a person experiences more stress, the tone of the person's voice becomes higher and the volume thereof becomes larger.

Figures 6, 7:
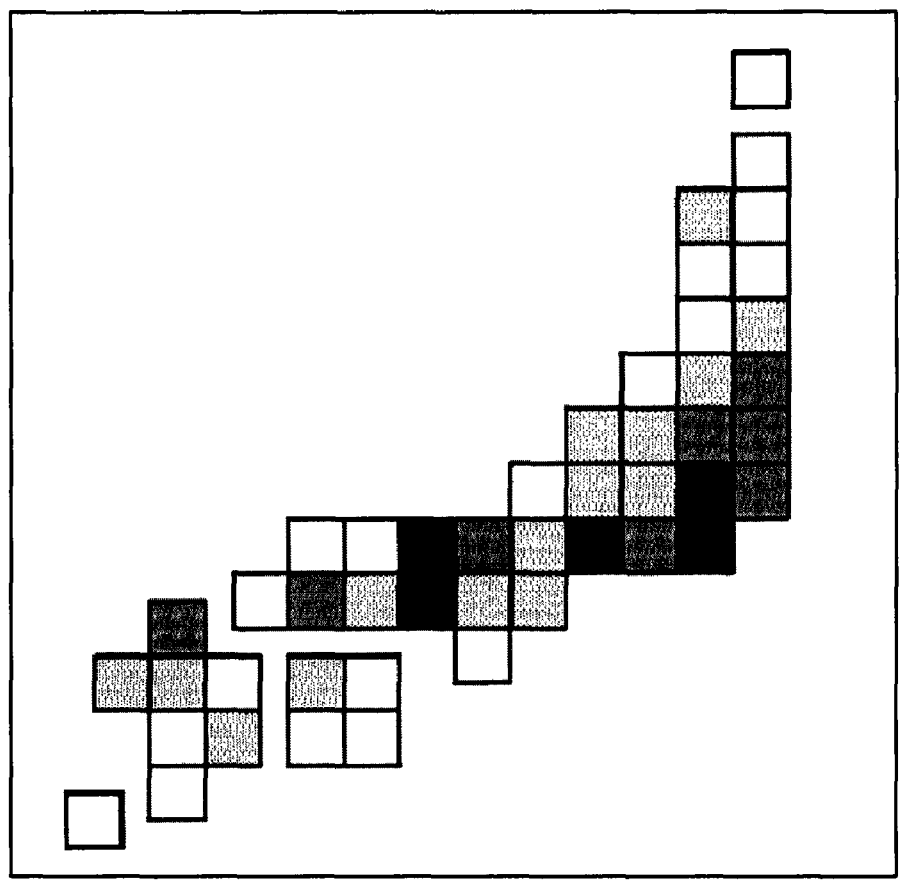
FIG. 6 is a diagram showing an example of a stress level determination table according to the present embodiment.
FIG. 7 is a diagram showing an example of displaying a stress level on a map or a layout diagram according to the present embodiment.

Specifically, as a power spectral density at high frequencies, the average of power spectral densities corresponding to frequencies greater than or equal to a threshold value (the mean power spectral density) is calculated for each combination of the acquired power spectral density and the position information. Then, if there are a plurality of combinations of the acquired power spectral density and the position information, the average of the mean power spectral densities of the plurality of combinations is calculated. Then, the stress level is determined according to the calculated average with reference to a stress level determination table, for example, as shown in FIG. 6.

Then, the stress level outputting unit 34 sends the obtained stress level in association with the designated area to the user terminal 14 (S205).

The user terminal 14 receives the stress level sent from the map server 13, and displays the stress level in association with the designated area on, for example, a display (S206).

As a display method, for example, it is conceivable that on a map of a predetermined area including the designated area, a stress level is displayed as a numerical value or a graph in association with the designated area, or the designated area is displayed with a color, a gray scale, a symbol, or the like corresponding to the stress level. FIG. 7 shows an example in which prefectures are designated as areas on a schematic Japanese map, and stress levels are displayed using a four-level gray scale.

The stress level outputting unit 34 may create map information for such display using an existing map information providing service or database as required, and send it to the user terminal 14.

The present disclosure is not limited to the above described embodiment, and various modifications, additions, and subtractions can be made by those skilled in the art without departing from the sprit and scope defined by the appended claims.

For example, the map server 13 may acquire a combination of a power spectral density and voice input position information from each of a plurality of types of mobile communication networks.

Further, for example, a part or all of the functions of the frequency power information calculating unit 21 and the data transmitting unit 22 of the center station 12 may be implemented in other devices (such as the mobile terminal 10, the base station 11, the map server 13, etc). Similarly, a part or all of the functions of the map server 13 may be implemented in other devices (such as the mobile terminal 10, the base station 11, the center station 12, the user terminal 14, etc). In this case, devices in which such functions are implemented in a distributed manner are configured to be able to communicate with each other. Additionally, the map server 13 is configured to be able to communicate with a device in which the data transmitting unit 22 and the like are implemented.

Further, although a stress level is obtained with respect to an area designated by a user in the above described embodiment, the present disclosure is not limited to such a configuration. For example, a map creation request including information for designating a map's scope and a unit area instead of area designation information may be sent from the user terminal 14. If default values are designated with respect to the map's scope and the unit area, just a map creation request may be sent. Upon receiving the stress level map creation request, the map server 13 obtains a stress level of each unit area (for example, prefecture) included in the designated map's scope (for example, the whole of Japan), and outputs the stress level in association with each respective unit area to the user terminal 14. In this case, in the map server 13, map information for displaying a stress level of each unit area on a map including the designated map's scope (see FIG. 7) may be created, and sent to the user terminal 14.

Further, a power spectral density is used as an example of frequency power information in the above described embodiment, other types of frequency power information such as an energy spectral density may be used to obtain a stress level.

Further, although a stress level is obtained when a stress level output request is received by the map server 13 in the above described embodiment, the map server 13 may obtain a stress level (processed information of a biological information) based on a power spectral density before receiving a stress level output request, and register the combination of the obtained stress level and voice input position information in the storing unit. In this case, in the stress level output phase, stress levels associated with position information related to a designated area with reference to the storing unit, and the average of the extracted stress levels (the individual feature about a user of the designated area) is calculated.

Further, although a mean power spectral density corresponding to frequencies greater than or equal to a threshold value is obtained by the stress level outputting unit 34 in the above described embodiment, the frequency power information calculating unit 21 and the data transmitting unit 22 may obtain a mean power spectral density corresponding to frequencies greater than or equal to a threshold value, and send the mean power spectral density in combination with voice input position information to the map server 13. In this case, the frequency power/position information acquiring unit 31 acquires the mean power spectral density as frequency power information, and registers it in association with the voice input position information in the frequency power information storing unit 32. Instead, the center station 12 may send a combination of voice information and voice input position information to the map server 13 without processing the voice information, and then the map server 13 may register the voice information or a power spectral density calculated based on the voice information in association with the voice input position information in the storing unit.

Further, although a threshold value as described above can be preset in the stress level outputting unit 34 according to a method of determining a stress level, a threshold value may be allowed to be changed by an administrator and the like of the information processing system 1 or by an instruction given from a user through the user terminal 14. In the latter case, the user selects a threshold value, and thereby a stress level dependent on a frequency domain desired by the user can be obtained. In addition, a stress level may be determined by obtaining a means power spectral density corresponding to frequencies less than or equal to a threshold value, or obtaining a means power spectral density corresponding to frequencies in a predetermined range by setting of a plurality of threshold values.

Further, although in the above described embodiment, position information of the base station 11 which relayed voice communication of the mobile terminal 10 when a voice was inputted to the mobile terminal 10 is used as position information of a user, position information of the mobile terminal 10 which was being registered in a home memory station when a voice was inputted to the mobile terminal 10 may be used as position information of the user. Alternatively, in a case where the mobile terminal 10 can perform radio communicate with two or more base stations 11 when a voice is inputted to the mobile terminal 10, the position of the mobile terminal 10 may be estimated based on a signal of the radio communication (for example, radio field intensity), and used as position information of the user.

Alternatively, in a case where the mobile terminal 10 has a GPS function, the position information of the mobile terminal 10 which is determined by the GPS function of the mobile terminal 10 within a period determined based on the time when a voice was inputted (for example, within the past one hour from the time when a voice was inputted) may used as position information of the user. Since a position resolution higher than that obtained using position information of a base station can be obtained if the GPS function is used, an area such as a floor or a room in a building can be designated as a unit to obtain a stress level. In this case, on a two or three-dimensional layout view of the building, a stress level may be displayed as a numerical value or a graph in association with the designated area, or the designated area may be displayed with a color, a gray scale, a symbol, or the like corresponding to the stress level.

Further, although a power spectral density of a user's voice inputted to the mobile terminal 10 is acquired in the above described embodiment, a power spectral density of a user's voice inputted to a device (for example, a fixedly installed microphone device) other than the mobile terminal 10 may be acquired. In this case, information of an installation position of the microphone device can be used as position information of the user.

Further, although a stress level is obtained based on a power spectral density of a voice in the above described embodiment, a different individual feature (for example, an excitement level) may be obtained based on frequency power information of the voice. For example, areas are set corresponding to attractions in an amusement park or the like, frequency power information of a spoken voice in the amusement park or the like and position information of a user determined by the above described GPS function are obtained, and an excitement level of each area is determined and displayed. Thereby, an interested party of the amusement park or the like can analyze an excitement level specific to each attraction.

Further, although a stress level is obtained based on a power spectral density of a voice in the above described embodiment, a stress level may be obtained based on other processed information based on a voice, for example, modulated information of a frequency.

Further, although a voice is used as biological information in the above described embodiment, a stress level or a different individual feature may be obtained using other types of biological information instead of or in addition to the voice. For example, biological information of a user (voice, blood pressure, pulse, perspiration, electrocardiogram, brain wave, bioelectric potential, oxygen saturation, body temperature, respiratory volume and frequency, the number of steps, etc.) or processed information thereof and the position information of the user at a time when the biological information was generated, may be acquired directly or indirectly from a potable monitoring device, and then individual features such as a stress level, an excitement level, a fitness level, and an exercise amount may be obtained and outputted (displayed) in association with a designated area.

The above described technical features of the embodiment and various modifications may be employed in any suitable combination.

What is claimed is:

1. An information processing system comprising:
    an acquisition unit which acquires a power spectral density of a voice inputted at a mobile terminal having a voice communication function, and position information of a base station device that relayed voice communication of said mobile terminal when said voice was inputted;
    a storage unit which stores said acquired power spectral density and said acquired position information in association with each other;
    an acceptance unit which accepts designation of an area; and
    an output unit which identifies the position information related to said designated area with reference to said storage unit, acquires the power spectral density associated with said identified position information, calculates the average of power spectral densities corresponding to frequencies greater than or equal to a threshold value (a mean power spectral density) for each combination of said acquired power spectral density and position information, calculates the average of the mean power spectral densities in said designated area, obtains a stress level of a user of said mobile terminal in said designated area based on said calculated average of the mean power spectral densities, and outputs the stress level in association with said designated area.

2. An information processing system comprising:
    an acquisition unit which acquires a power spectral density of a voice of a user, and position information of said user at a time when said voice was generated;
    a storage unit which stores said acquired power spectral density and said acquired position information in association with each other; and
    a feature output unit which identifies the position information related to a predetermined area with reference to said storage unit, acquires the power spectral density associated with said identified position information, calculates the average of power spectral densities corresponding to frequencies greater than or equal to a threshold value (a mean power spectral density) for each combination of said acquired power spectral density and position information, calculates the average of the mean power spectral densities in said predetermined area, obtains an individual feature about the user in said predetermined area based on said calculated average of the mean power spectral densities, and outputs the individual feature in association with said predetermined area.

3. The information processing system according to claim 2, wherein said acquisition unit acquires, as a power spectral density of a voice of said user, a power spectral density of a voice of said user which was inputted at a mobile terminal having a voice communication function, and acquires, as the position information of said user, position information of said mobile terminal at a time when said voice was inputted.

4. The information processing system according to claim 3, wherein said acquisition unit acquires, as the position information of said mobile terminal, position information of a base station device that relayed voice communication of said mobile terminal when said voice was inputted, or position information of said mobile terminal which is determined by a GPS function of said mobile terminal within a period determined based on the time when said voice was inputted.

5. The information processing system according to claim 3, wherein said feature output unit obtains a stress level of the user of said mobile terminal in said predetermined area as said individual feature based on the average of the mean power spectral densities, and outputs the stress level in association with said predetermined area.

6. The information processing system according to claim 2, wherein said feature output unit outputs map information for displaying said individual feature in association with said predetermined area on a map or a layout diagram of a scope including said predetermined area.

7. An operating method of a computer, wherein
    said computer acquires a power spectral density of a voice inputted at a mobile terminal having a voice communication function, and position information of a base station device that relayed voice communication of said mobile terminal when said voice was inputted;

said computer stores said acquired power spectral density and said acquired position information in association with each other in a memory;

said computer accepts designation of an area; and said computer identifies the position information related to said designated area with reference to said memory, acquires the power spectral density associated with said identified position information, calculates the average of power spectral densities corresponding to frequencies greater than or equal to a threshold value (a mean power spectral density) for each combination of said acquired power spectral density and position information, calculates the average of the mean power spectral densities in said designated area, determines a stress level of a user of said mobile terminal in said designated area corresponding to said calculated average of the mean power spectral densities with reference to a stress level determination table in which correspondence relationship of the average of the mean power spectral densities and the stress level is defined, and outputs the stress level in association with said designated area.

* * * * *